(12) United States Patent
Pitt

(10) Patent No.: US 11,166,861 B2
(45) Date of Patent: Nov. 9, 2021

(54) METHOD OF SPECIFYING A CUSTOMIZED WHEELCHAIR USING A MEASUREMENT JIG AND COMPUTER-IMPLEMENTED MODEL GENERATION DEVICE

(71) Applicant: Roma Medical Aids Limited, Mid Glamorgan (GB)

(72) Inventor: John Pitt, Bridgend (GB)

(73) Assignee: Roma Medical Aids Limited, Bridgend (GB)

( * ) Notice: Subject to any disclaimer, the term of this patent is extended or adjusted under 35 U.S.C. 154(b) by 80 days.

(21) Appl. No.: 14/443,112

(22) PCT Filed: Nov. 8, 2013

(86) PCT No.: PCT/GB2013/052944
§ 371 (c)(1),
(2) Date: May 15, 2015

(87) PCT Pub. No.: WO2014/076457
PCT Pub. Date: May 22, 2014

(65) Prior Publication Data
US 2015/0297429 A1    Oct. 22, 2015

(30) Foreign Application Priority Data

Nov. 16, 2012 (GB) ..................................... 1220645
Apr. 30, 2013 (GB) ..................................... 1307769

(51) Int. Cl.
*A61B 5/107* (2006.01)
*A61G 5/10* (2006.01)
(Continued)

(52) U.S. Cl.
CPC ................ *A61G 5/10* (2013.01); *A61B 5/107* (2013.01); *A61B 5/1072* (2013.01);
(Continued)

(58) Field of Classification Search
USPC ................................................. 700/95–212
See application file for complete search history.

(56) References Cited

U.S. PATENT DOCUMENTS 4,728,150 A * 3/1988 Gaudreau, Jr. ........ A47C 1/023
297/284.1
4,890,235 A 12/1989 Reger
(Continued)

FOREIGN PATENT DOCUMENTS

CN    201897528 U    7/2011
EP    2116153 A1    11/2009
(Continued)

OTHER PUBLICATIONS

Kumar, V., Rahman, T. and Krovi, V. 1999. Assistive Devices For Motor Disabilities. Wiley Encyclopedia of Electrical and Electronics Engineering.*

(Continued)

*Primary Examiner* — Kenneth M Lo
*Assistant Examiner* — Istiaque Ahmed
(74) *Attorney, Agent, or Firm* — Gordon & Jacobson, P.C.

(57) ABSTRACT

The invention provides a measurement apparatus (jig) comprising at least one adjustable component to enable at least one measurement to be taken for bespoke configuration of customised seated user equipment (such as a wheelchair). It is particularly suited for use in the design or construction of a sporting wheelchair or disabled apparatus. The jig may comprise part of a system comprising measuring means for taking measurements relating to the set configuration of adjustable components of the jig. The measuring means may comprise electronic or optical means, such as position sensors, pressure sensors, or a camera. The system may also comprise a computer-implemented modelling component arranged to generate a visual representation of the cust- (Continued)

omised wheelchair or other appliance constructed in accordance with the set configuration of adjustable components of the jig.

6 Claims, 11 Drawing Sheets

(51) Int. Cl.
  *G06F 30/00* (2020.01)
  *G05B 19/4097* (2006.01)
(52) U.S. Cl.
  CPC ......... *G05B 19/4097* (2013.01); *G06F 30/00* (2020.01); *A61B 2505/09* (2013.01)

(56) References Cited

U.S. PATENT DOCUMENTS

| | | | | |
|---|---|---|---|---|
| 4,972,351 | A | | 11/1990 | Reger |
| 4,993,164 | A | * | 2/1991 | Jacobsen ............... A47C 7/46 297/284.4 |
| 5,642,302 | A | * | 6/1997 | Dumont ............... B60N 2/0232 128/845 |
| 2007/0021858 | A1 | * | 1/2007 | Slemker ............... A61B 5/107 700/118 |
| 2010/0073685 | A1 | | 3/2010 | Trenkenschu |
| 2012/0126450 | A1 | | 5/2012 | Van Berkum |

FOREIGN PATENT DOCUMENTS

| | | |
|---|---|---|
| JP | 2002045403 | 12/2002 |
| NL | 1005567 C1 | 9/1998 |
| TW | 201029645 A | 8/2010 |
| WO | WO 2012/144858 A2 | 10/2012 |

OTHER PUBLICATIONS

Graham, Wheelchair Animation in Daz3D, Apr. 9, 2012, [retrieved on Jul. 22, 2016] Retrieved from the Internet: <URL:http://www.streetsie.com/wheelchair-animation-daz3d/>.*

Greg Saul, Manfred Lau, Jun Mitani, and Takeo Igarashi. 2010. SketchChair: an all-in-one chair design system for end users. In Proceedings of the fifth international conference on Tangible, embedded, and embodied interaction (TEI '11). ACM, New York, NY, USA, 73-80. DOI=http://dx.doi.org/10.1145/1935701.1935717.*

"Computer-Aided Design in Wheelchair Seating", Marc St-Georges et al., Department of Veterans Affairs, Journal of Rehabilitation Research and Development, vol. 26 No. 4 pp. 23-30, Fall 1989.

* cited by examiner

Design Table for: DEFCHAIR2

| $DESCRIPTION | Wheel @ S-Seat+Axle | Cambre @ S-Seat+Axle | Seat Width@ S-Seat+Axle | Seat Height@ S-Seat+Axle | Seat Angle@ Centre | Seat Length@ Centre | Wheel in | Cambre | Seat Width | Seat Height | Seat Angle | Seat Length | Antitip Height |
|---|---|---|---|---|---|---|---|---|---|---|---|---|---|
| Default <As Machined> | 635 | 18 | 381 | 375 | 20 | 320 | | | | | | | |
| Default <As Welded> | 533.4 | | 457.2 | | | | | | | | | | |
| 21 Wheel | 533.4 | 20 | 381 | 355.6 | 25 | 355.6 | 21 | 20 | 16 | 14 | 25 | 14 | 15 |
| 22 Wheel | 558.8 | 18 | 381 | 330.2 | 20 | 342.9 | 22 | 18 | 16 | 13 | 20 | 13.5 | 10 |
| 23 Wheel | 584.2 | 20 | 457.2 | 342.9 | 19 | 381 | 23 | 20 | 19 | 13.5 | 19 | 15 | 5 |
| 24 Wheel | 609.6 | 19 | 406.4 | 355.6 | 20 | 342.9 | 24 | 19 | 17 | 14 | 20 | 13.5 | 0 |
| 25 Wheel | 635 | 20 | 406.4 | 381 | 19 | 330.2 | 25 | 20 | 17 | 15 | 19 | 13 | 20 |
| 26 Wheel | 660.4 | 18 | 431.8 | 406.4 | 18 | 355.6 | 26 | 18 | 18 | 16 | 18 | 14 | 5 |
| 26 Wheel2 | 609.6 | 28 | 334.645 | 406.4 | 12 | 355.6 | 24 | 28 | 14.175 | 16 | 12 | 14 | 0 |
| Test | 609.6 | 24 | 355.6 | 406.4 | 12 | 355.6 | 24 | 24 | 15 | 16 | 12 | 14 | 5 |
| Test 2 | 609.6 | 22 | 533.4 | 406.4 | 18 | 355.6 | 24 | 22 | 22 | 16 | 18 | 14 | 5 |
| Test 3 | 609.6 | 24 | 431.8 | 406.4 | 20 | 381 | 24 | 24 | 18 | 16 | 20 | 15 | 5 |

FIG. 11

METHOD OF SPECIFYING A CUSTOMIZED WHEELCHAIR USING A MEASUREMENT JIG AND COMPUTER-IMPLEMENTED MODEL GENERATION DEVICE

CROSS-REFERENCE TO RELATED APPLICATIONS

This application is the national stage of International Patent Application No. PCT/GB2013/052944 filed on Nov. 8, 2013, which claims priority to British Patent Application No. GB 1220645.4 filed on Nov. 16, 2012, and to British Patent Application No. GB 1307769.8 filed on Apr. 30, 2013, all of which are hereby incorporated by reference in their entireties as if fully set forth herein.

BACKGROUND

1. Field

This invention relates generally to measuring devices, and more particularly to tools for measuring and/or recording the geometrical requirements of customised seated user equipment, to customise the equipment to the individual needs of a user. The invention is particularly suited, but not limited to, use in the design and manufacture of wheelchairs.

2. Related Art

Wheelchairs can vary enormously in design and specification due to the wide variety of users' needs, and the types of activity that the chairs are used for. For example, there are bariatric wheelchairs, pediatric wheelchairs, lightweight 'transit' wheelchairs and so on. Wheelchairs may be manually propelled or motorised.

In addition to 'everyday use' wheelchairs, various types of sports wheelchairs are available which enable the occupant to participate in a disabled sporting activity such as rugby, tennis, racing and basketball. Sports wheelchairs are usually designed to provide speed, agility, low weight and/or maximum strength, and different wheelchair sports often require specific configurations.

A typical manually-propelled wheelchair incorporates a seat or platform for supporting the occupant, a back rest which the occupant leans against, one or more foot rests and four wheels: two smaller wheels at the front and two large wheels at the back. The two larger wheels are usually provided with hand rims which the occupant grips and pushes to propel the chair. Two push handles at the top of the back to allow the chair to be pushed by an assistant or carer. However, wheelchairs often vary greatly in design and specification.

Different disabilities give rise to different needs which must be catered for by the design of the chair. For example, a user whose body weight rests more naturally to one side more than the other may develop pressure sores unless the occupant's sitting position is taken into consideration in the design of the chair.

Different uses (e.g. sports versus everyday) also affect the design and specification of a wheelchair. For example, with sports wheel chairs a snug rather than loose fit for the occupant may be important not only for the sake of comfort but also for enhanced sporting performance or safety.

Therefore, it is highly desirable to customise the wheelchair according to the user's particular and individual needs. Such customisations may, for example, include tailoring the seat dimensions to the user's physical proportions; other variants may include the height of the seat and/or back rest, angle of the seat and/or backrest, footrests, leg rests, front wheel support mechanisms and so on.

At present, when a user wishes to order a customised wheelchair from a manufacturer, the manufacturer provides a form which the user completes and returns. The form includes a list of items for which the user must supply a measurement. For example, the user will need to specify the length, width, height and angle of the seat; the distance between the wheels, the foot plate position, pivot centres and potentially much more.

While this is a difficult and daunting enough task for the user if he has a current wheelchair against which to compare and calculate the desired parameters, the task becomes even more difficult if the user is attempting to specify the requirements of his first chair. In many cases, the user resorts to estimating or guessing the required geometry of the desired chair.

Once the form is complete it is returned to the manufacturer who then constructs a chair according to the parameters specified by the user for the various components.

Given the imprecise, difficult and time consuming nature of the specification process, it is not uncommon to find that the end result is a less than ideal configuration for the wheelchair user's needs. It may be that it does not physically accommodate the user as well as it could or should, or does not provide the functionality that the user requires. Therefore, comfort, safety or performance may be less than optimal. In many cases, the chair is not used by the user due to the discomfort it gives rise to or other lack of suitability. However, as the manufacturer has correctly provided the chair in accordance with the specified requirements, it cannot be returned or refunded. Therefore, this procurement process can be a costly, disappointing and inconvenient experience for the wheelchair user.

Thus, it is desirable to provide a solution which enables a user to specify the geometrical requirements of a customised invalid appliance (e.g. a wheelchair, disabled sporting appliance, invalid chair etc.) accurately and easily such that the design of the resulting appliance is enhanced in respect of the user's individual needs. It is also desirable to provide a solution which facilitates the appliance manufacture process by enabling the measurements of an individual user or the components of his desired wheelchair to be taken easily, quickly and accurately. Further still, it is desirable to provide a solution which would enable a user to gain a view or perspective of how a particular appliance e.g. wheelchair, made to specified measurements, would accommodate him.

Such an improved solution has now been devised.

SUMMARY

Thus, in accordance with the present invention there is provided a measurement jig as claimed herein. The invention may be described as a measuring apparatus arranged to record at least one attribute pertaining to one or more components of a bespoke chair or seated appliance, such as wheelchair, disabled sporting appliance or invalid chair. The apparatus may provide a design or specification from which the chair can be constructed, thus enabling the appliance to be tailored to meet the functional requirements and/or physical attributes of a given user. For the sake of convenience, the appliance may be referred to as a 'wheelchair' herein.

Thus, a measurement jig may be provided, comprising at least one adjustable component to enable at least one measurement to be taken for bespoke configuration of a seated user equipment (such as a wheelchair, sporting appliance for a disabled user, invalid chair etc.).

The adjustable component may be any component which is known to be provided on or in a wheelchair. For example, an arm rest, a back rest, and foot plate, a seat etc. The component is adjustable in that at least one parameter relating to the component can be altered. For example, a parameter relating to its position, orientation, geometric properties, appearance etc.

The jig may or may not comprise all features or components which may be known in conjunction with a wheelchair. For example, in some embodiments the jig may not comprise wheels.

A component may be adjustable in more than one way. For example, the seat support platform may be tiltable as well as slidable. Thus, more than one parameter may be altered in relation to the same component.

The jig may be configured such that an individual is able to sit on and/or in the jig. Therefore, the jig may comprise a seat or chair component.

The adjustable component may comprise sub-components. For example, the seat may comprise a support platform (i.e. a base upon which the user rests), one or more side walls and/or a back rest. One or more of the sub-components may be adjustable.

There may be a plurality of different types of adjustable components provided on the jig. Each of the adjustable components may be adjustable in a different way. For example, the back rest may be tiltable whilst the seat may be slidable in the horizontal or vertical plane (forwards/backwards, up/down).

The adjustable component may be a support element configured to support a portion of an individual's body. For example, the support element may be:
  i) a seat upon which the individual sits;
  ii) a side wall against which an individual can lean;
  iii) an arm, foot, head or back rest; or
  iv) other support element upon or against which an individual can rest a portion of his body.

Preferably, the jig comprises a frame, the adjustable component being mounted on or carried by the frame. The adjustable component may be moveable relative to the frame. The frame may be constructed from a plurality of tubular elements.

Preferably, the adjustable component may be adjustable by rotational, vertical, horizontal or angular displacement. The component may be displaced in some manner from a starting position to a finishing position. For example, the seat may be moveable toward the front of the wheelchair or towards the back; the head rest may be tiltable.

The jig may comprise means for measuring a defined set of geometric (or other) parameters e.g. relating to the size, position, angle or orientation of the adjustable component relative to a predetermined reference point. The reference point may be the floor or another component of the jig. For example, the height of the seat may be measured from the floor; or the angle of the foot rest may be measured relative to a support arm on the jig; or the distance between the side walls of the seat may be measured.

Preferably, an adjustment means is provided to enable adjustment of the adjustable component. The adjustment means may be a mechanical device or system. For example, the adjustment means may be a threaded screw attached to the component; or a slidable collar which may be clamped at a desired position along the length of a post. The adjustable component may be manually adjustable (e.g. slidable upon being pushed by a human technician).

In certain embodiments the adjustment means may be powered. Electromechanical drives such as stepping motor drives or solenoid actuators may be used, for example. The adjustment means may be powered to be adjustable by a controller, such as a handheld controller arranged to operate most of or all the adjustable components. This enables the user to re-configure the jig themself to the most comfortable or accommodating position.

The adjustable component may be configured for adjustment under the direction of an automated control (adjustment) means. The adjustment means may comprise an electronic component. The adjustment means may comprise instructions executing on the processor of a computer-implemented device or system.

The adjustment means may be arranged and configured to enable the adjustable component to be adjusted remotely. For example, the adjustment means may comprise an electronic control device which a technician operates, possibly through the use of push buttons, to re-orientate an adjustable component. The control device may be arranged for wireless or wired communication with the jig so as to perform adjustment of one or more components. Additionally or alternatively, the control device may be arranged for mechanical or electronic communication with the jig.

The adjustment means may be controlled by a computerised system executing software to monitor, control and/or alter one or more parameters pertaining to one or more adjustable components.

The means for measuring or recording the values of the parameters may take any suitable form or implementation.

The jig may include one or more readable measurement means mounted on/in, or carried upon, the jig. The measurement means may be a mechanical device. For example, a ruler or measuring gauge may be provided on the frame of the jig so that displacement of a component from a starting position to a finishing position can be measured in centimetres. The measurement may be read manually or by automated measuring means. The term 'manually' is used herein to mean that the measurement is captured 'by a human' e.g. a visual reading may be performed by a technician. The term 'automated means' is used herein to mean some non-human (mechanical or electronic) arrangement (device or system) is used to take the reading (i.e. obtain the value for the parameter).

Thus, a device may be used to generate the geometric, positional or other attribute data relating to the adjusted (finishing) configuration of the component. The automated measuring arrangement may be computerised, and the data may be in digital form.

Also in accordance with the present invention, there is provided a method of specifying the configuration of a seated invalid appliance, such as a wheelchair, invalid chair, disabled sporting equipment; the appliance having a plurality of components, and the method comprising the step:
  providing a jig according to any embodiment described above; and/or
  using a jig according to any embodiment described above to derive at least one measurement relating to an attribute (size, position, orientation or other configuration) of at least one of the appliance components.

Preferably, the method may further comprise the steps of:
  seating an individual upon a seat provided on or in the jig;
  adjusting the at least one adjustable component in response to one or more instructions received from the individual;
  recording data relating to the adjustment.

Preferably, the method may further comprise the step of:
  communicating the recorded data to a destination for use in the construction, reconfiguration or computerised modelling of a seated invalid appliance.

Thus, the invention may comprise an apparatus and corresponding method which facilitates the specification of the geometrical and other requirements of a customised wheelchair (or other seated invalid appliance) accurately and easily such that the design of an appliance constructed or adapted in accordance with the specified requirements is optimised or at least enhanced with respect to the user's individual needs.

In one sense, the jig provides a malleable model (i.e. abstracted version) of an appliance in which the user can sit while one or more of the components are adjusted around him. This allows the user to experiment with various sitting positions, angles, sizes, relative compositions of components prior to committing himself to a particular appliance specification. The jig provides some insight into how a 'real' appliance configured in this manner would feel and/or perform. In turn, this enables the user to provide feedback and/or instructions regarding the acceptability of the configuration to a technician.

According to a further aspect, there is provided a system for specifying the configuration of a customised seated invalid equipment (such as a wheelchair, disabled sporting appliance, etc), the system comprising a jig according to any embodiment described above, and one or more measuring means for taking at least one measurement relating to the adjusted configuration of at least one adjustable component of the jig.

The measuring means may comprise a gauge or ruler, or may comprise electronic or optical means, such as a position sensor, pressure sensor or a camera.

The measuring means may be configured to generate and gather data relating to at least one parameter pertaining to at least one adjustable component of the jig such that a wheelchair (or at least a wheelchair component) can be constructed using that data.

Preferably, the system further comprises a computer-implemented modelling component configured to receive the data relating to the at least one parameter. The data may be received from the measuring means. The data may be received in electronic form from the measuring means. The data may be in digital form.

The modelling component may be a computer system comprising a CPU, software configured to execute upon the CPU, and associated volatile and non-volatile storage. The modelling component may be configured to store the data for future reference. The data may be stored in association with the individual user.

Preferably, the modelling component comprises software arranged to generate a visual representation of a wheelchair or other appliance constructed in accordance with the adjusted configuration of the jig components. The visual representation may be a 2-D image or a 3-D model. The advantage of this feature is that the user is able to see a predicted view of how the bespoke wheelchair will look.

The representation may be generated using data generated by the measuring means. In essence, the user-specific data can be automatically generated by the invention and fed into the modelling and subsequent manufacturing processes. This provides the advantage that the measuring process is made easier. It can also be performed more quickly. It can also assist in reducing the likelihood of user error when taking and manually entering the data.

The modelling component may be configured to receive user-related data relating to the physical attributes of the user. For example, arm length, length leg, height, weight etc. This user-related data may be used to generate a model of the user. The modelling component may be arranged to generate a visual representation (e.g. 3-D model or 2-D image) of the user sitting in a bespoke wheelchair constructed according to the adjusted configuration of the jig. The advantage of this feature is that it provides the user with a more detailed prediction of how the bespoke wheelchair will accommodate him if constructed according to those parameters. For example, if the user sees from the model that his knees will be raised when sitting in the chair, he may request that the footrest be lowered or the seat platform be raised. The representation may be re-generated after further adjustment of the jig and/or alteration of the data.

The invention may be used to specify the desired properties of at least one component of a new invalid appliance which is to be built according to the determined specification, or may be used to adapt, adjust or reconfigure an existing appliance so that it better meets the physical or performance needs of the individual (user).

The invention provides the advantage that the user can physically sit in or on the jig and provide feedback relating to the acceptability of the jig's configuration; the user's approved jig configuration can then be emulated during the configuration of an actual appliance such that the same approved properties are reproduced in the resulting appliance. This eliminates the need to guess or estimate the specifications and increases the likelihood that the appliance will meet the user's requirements.

These and other aspects of the present invention will be apparent from and elucidated with reference to, the embodiment described herein.

BRIEF DESCRIPTION OF THE DRAWINGS

An embodiment of the present invention will now be described, by way of example only, and with reference to the accompanying drawings.

FIG. 11 shows a design table having been populated with data specifying the dimensions and properties of the various wheelchair components. This data can then be used to generate the models shown in FIGS. 6 to 10.

DETAILED DESCRIPTION

Figure 1:
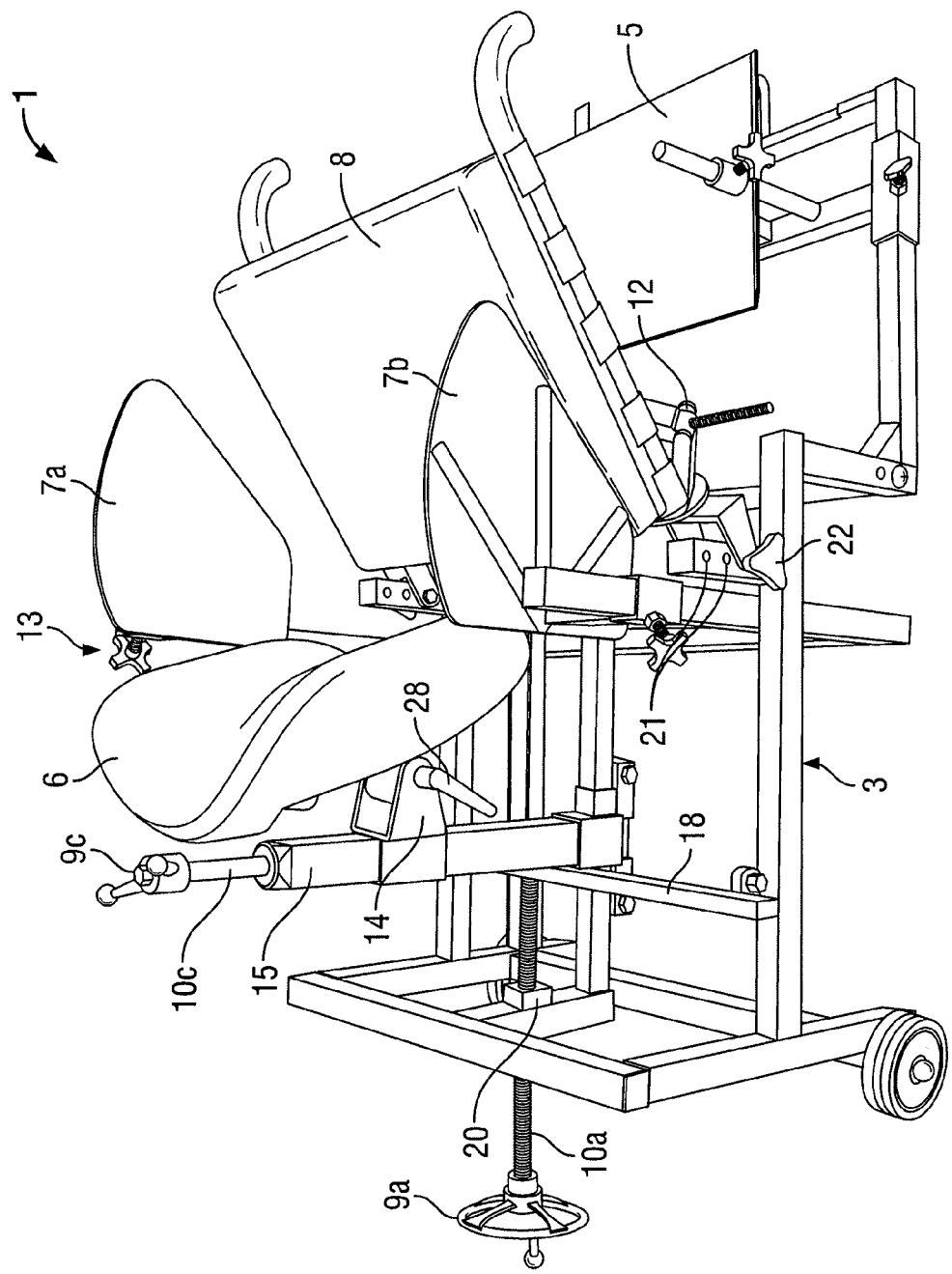
FIGS. 1 to 5 illustrate various views of a jig in accordance with an illustrative embodiment of the invention.
Figure 2:
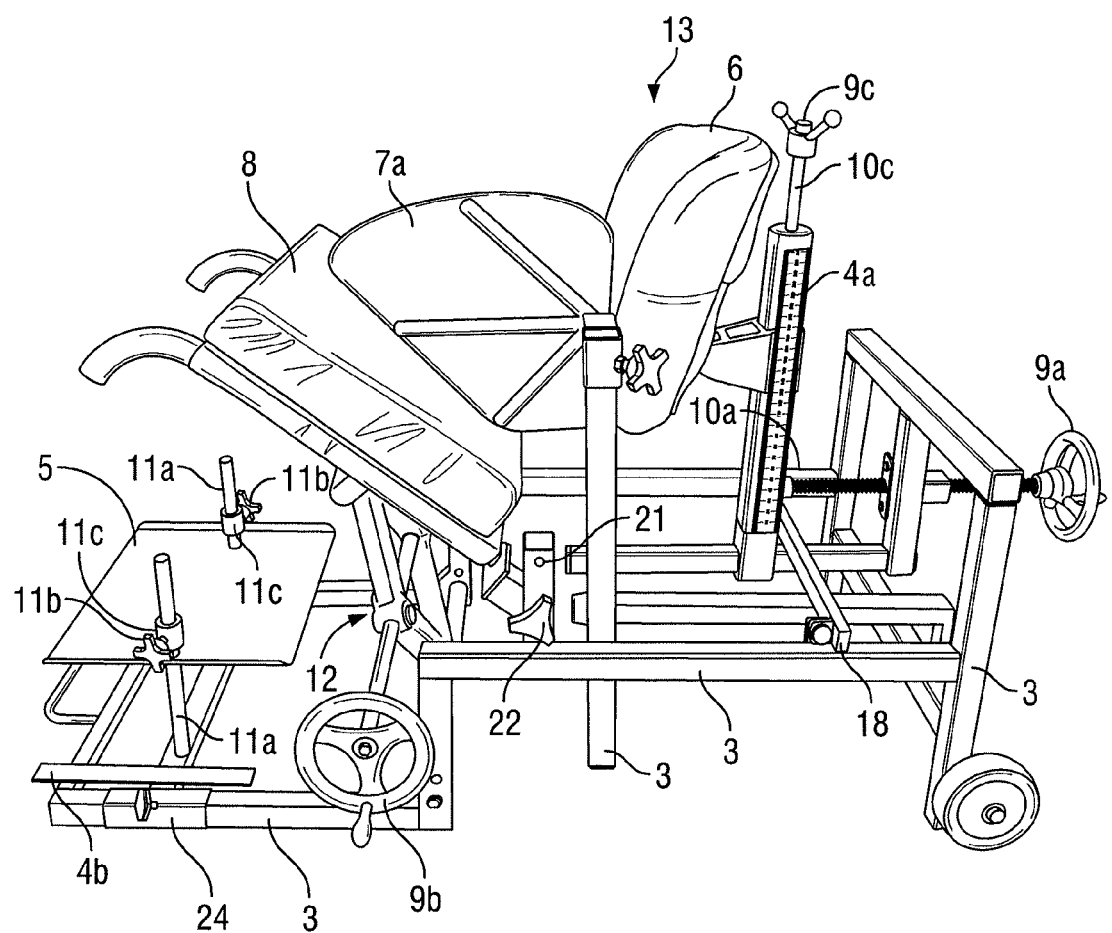
Figure 3:
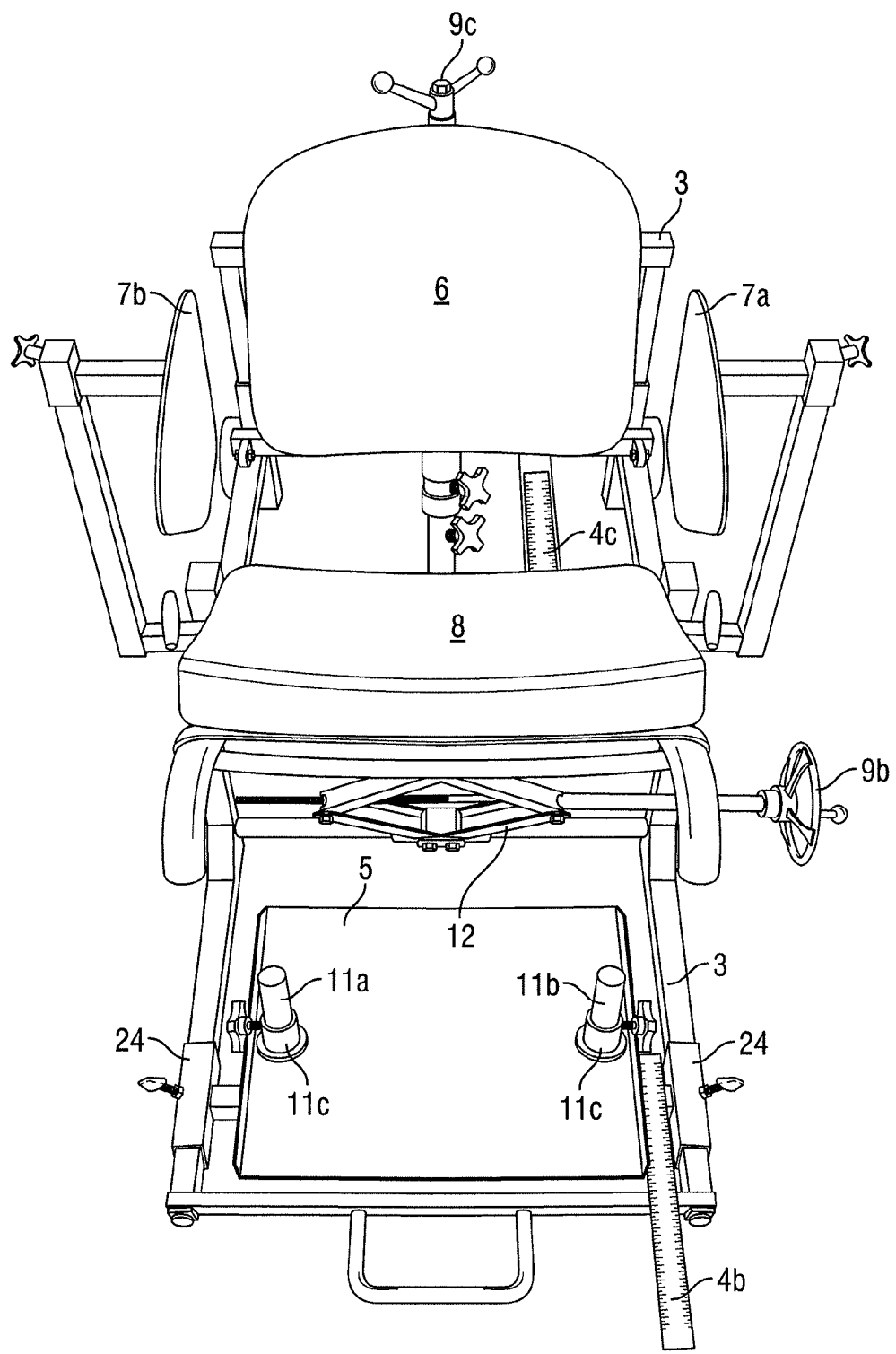
Figure 4:
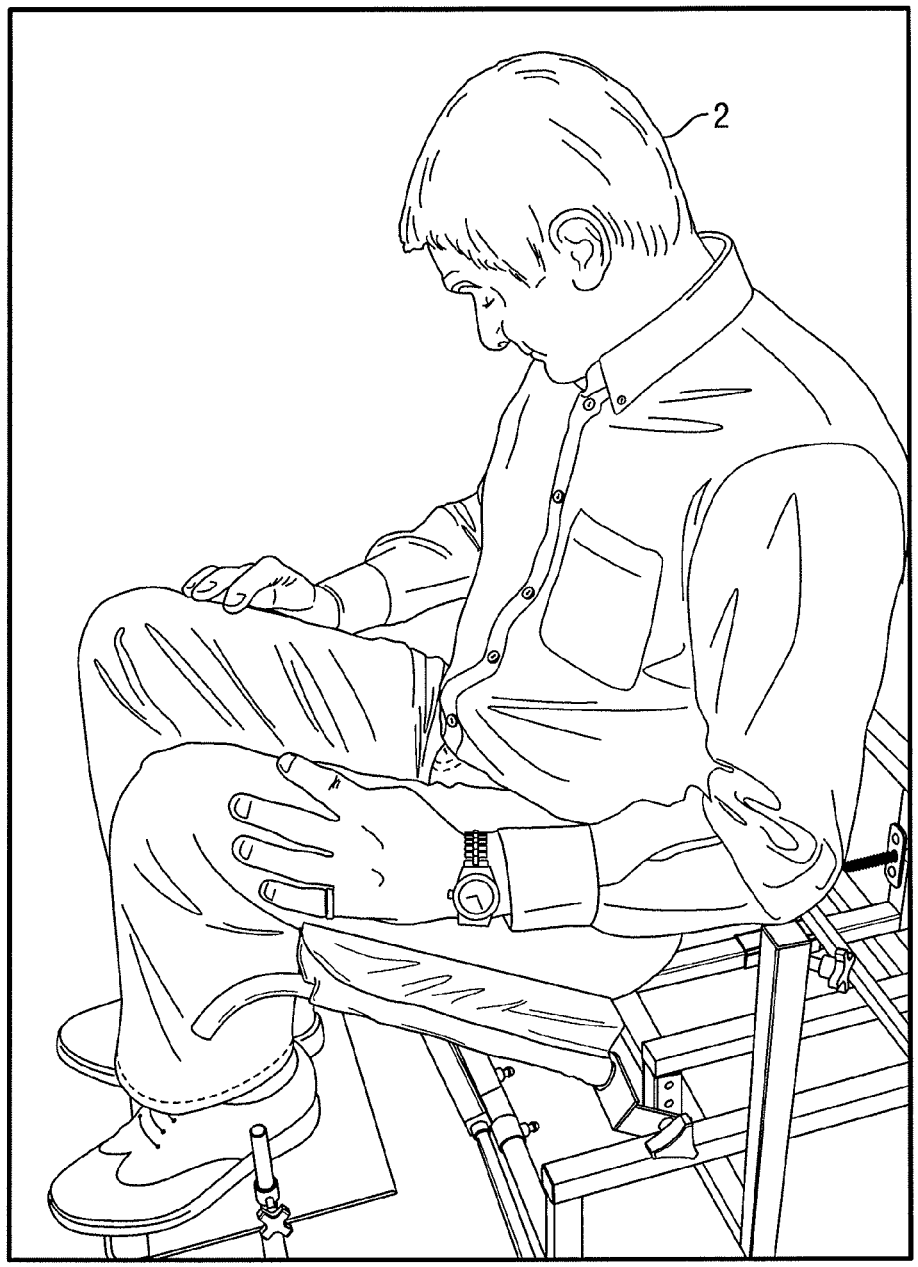
Figure 5:
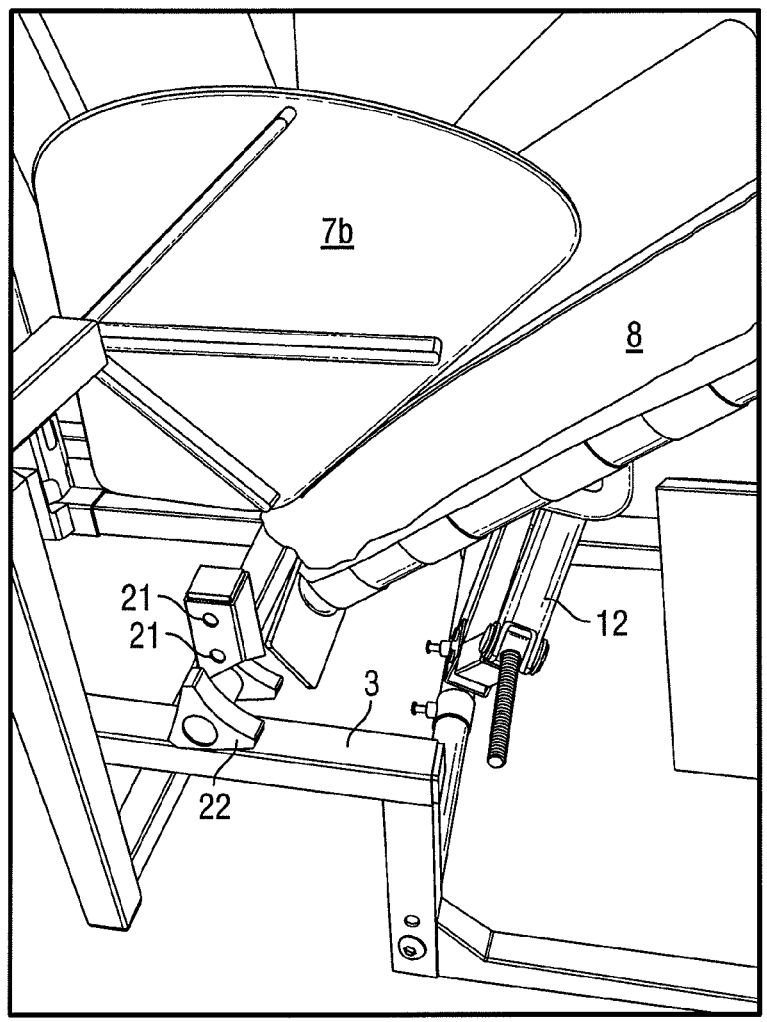

The figures show an illustrative embodiment of an inventive measuring jig 1 which an individual 2 can use to ascertain the features and properties he desires in a wheelchair. In essence, the invention 1 comprises a support frame 3 upon which are mounted various components typically provided on a known wheelchair. In the exemplary embodiment, these include a seat base (or support platform) 8, a foot rest 5, a backrest 6, one or more arm rests 7a, 7b. In the drawings, the arm rests 7a, 7b are shown as side walls or panels between which the user sits on the seat base 8. However, in some embodiments the side walls and arm rests may be provided as separate (and possibly independently adjustable) components. The arm rests 7a, 7b can be thought of as 'support elements' as they support the user 2 as he leans against them or rests upon them while sitting in the jig 1.

It should be noted that other components may be provided on the jig. The invention is not intended to be limited in respect of the number, nature or purpose of the adjustable components.

The components are adjustable in their orientation, size, configuration and/or position. For example, backrest 6 can be adjusted to move horizontally, vertically and also tiltable between a substantially upright position relative to the floor and an inclined position.

The adjustment can be achieved using a variety of techniques or mechanisms. Manually operated actuator means (e.g. screw threaded jack 12 operated by handle 9b) are shown in the figures, but powered, computer-implemented means could be employed in addition to, or instead of, manually operated actuator devices. The jig is capable of being maintained in its 'set' position once all the adjustments are completed and measurement data can be extracted by either manually measuring pre-defined characteristics or determining the measurements automatically for example by viewing with a camera connected to appropriate computer software to extract the measurements.

In the specific embodiment shown, measuring devices 4a, 4b, 4c are provided on the jig. In practice, these may take any form necessary but may be, for example, a ruler, a pressure sensor, a balance, a calliper, or any sort of gauge. In the drawings, gauge rulers 4a, 4b and 4c are shown which can be used to provide data relating to the desired position of the associated adjustable components. In addition, the tilt of the seat portion 8 can be measured by means of a gauge on the jack 12.

In use, the user 2, for whom the wheelchair is to be customised, sits in the seat 13 of the jig 1. The user's sitting position and stance can be observed (manually or by computerised means). The components of the jig are then adjusted according to the user's needs and feedback. For example, the user may indicate that the back rest 6 is too upright and needs to be tilted backwards to provide a more comfortable seating position; or the user 2 may wish to have a more snug fit within the confines of the chair, and so the side walls 7a, 7b of the chair may be brought closer together towards each other (and the user's body therebetween).

The components may need to be adjusted in response to the user's physical measurements (.e. height, weight, leg length), or in response to the user's advice (e.g. "the back rest feels too upright" or my knees feel too elevated", so the foot rest 5 needs to be lowered).

The adjustment may be achieved by any suitable mechanism which enables manipulation of the relevant component.

In the embodiment shown in the drawings, the seatback portion 6 can be pushed/pulled towards the front or back of the jig 1 because it is supported on the sliding support post 15 which slides forwards and backwards relative to frame 3. Gauge rule 4c enables the forward/backward displacement of the seat to be measured and recorded by visual inspection of the position of cross member 18 which is connected to the support post 15. In response to feedback provided by the user 2, the technician turns the handle 9a which causes the seat back arrangement 6 to be propelled forwards or backwards depending on the direction in which the handle 9a is rotated. As handle 9a is rotated, the threaded shafted 10a to which it is connected also rotates. This shaft 10a extends through a threaded bore in boss 20 mounted on the frame 3 and can be rotated until the desired position of the seat back is reached. The end of the shaft 10a is connected to the support post 15 which therefore moves forward or backward relative to the frame as the shaft 10a rotates. The gauge 4c can then be inspected to provide data which can be used to record the set position of the seat back 6.

The backrest portion 6 of the chair 13 is lowered or raised by operation of actuator handle 9c rotating shaft 10c which is received in a threaded bore of the seat carrier 14, which consequently slides up or down the support post 15, depending upon the direction of rotation of the handle 10c. Once in the desired height position, the seat height dimension can be read from rule 4a which is mounted to the support post 15. The seat back 6 can be tilted by releasing the lever 28, tilting to the seat back 6 to the desired orientation and securing once more by re-tightening the lever 28.

The position of attachment of the rear of the seat portion 8 of the chair is raised or lowered relative to the frame by having a respective pivot formation secured in one of a plurality of vertically spaced apertures 21. The handles 22 are spring loaded and can be pulled outwardly to disengage the pivot formation from the respective aperture 21 to permit raising or lowering. The screw threaded jack 12 operated by handle 9b is used to alter the angle of tilt of the seat portion 8.

Considering the footrest 5 shown in the drawings, the footrest is adjustable in terms of angular, vertical and horizontal displacement. In other words, it can be tilted, lowered/raised and moved forwards/backwards. The footrest is attached to a pair of substantially vertical support posts 11a which pass through the footrest 5. A pair of slidable collars 11c connected to the foot rest 5 can be clamped to the posts 11a via a screw 11b passing through the collar 11c. The footrest can be moved forward or backward on the support frame 3 by means of being supported on sliding sections 24 capable of sliding on the frame 3. The gauge rule 4b measures the forward position of the footrest 5.

When a component has been moved into the desired position, data is taken to record that configuration. This may be done manually by observing a dial, ruler, gauge or some other measuring device and making a note of the data. This data may be filled into a manufacturer's order form on paper, or entered into a computerised system.

In certain embodiments the adjustment of the various components may be powered. Electromechanical drives such as stepping motor drives or solenoid actuators may be used, for example. The adjustment may be powered to be adjustable by a controller, such as a handheld controller arranged to operate most of or all the adjustable components. This enables the user to re-configure the jig themself to the most comfortable or accommodating position.

In some embodiments of the invention, the data from the measuring devices may not be collected manually. The collection of the data may be performed automatically and/or electronically, and may be fed into a computerised system for processing and/or transmission elsewhere.

For example, the means for taking measurements relating to the set position of adjustable components of the jig may comprise electronic or optical means, such as position sensors, or a camera. The data may be fed into a Computer-Aided Design (CAD) system. FIG. 11 shows a table which has been populated with data. The data specifies the properties (e.g. length, angle etc) of various wheelchair components. All or some of the data has been derived from the measuring jig. The data specifies the exact requirements of the customise wheelchair according to the user's needs or preferences.

Figure 6:
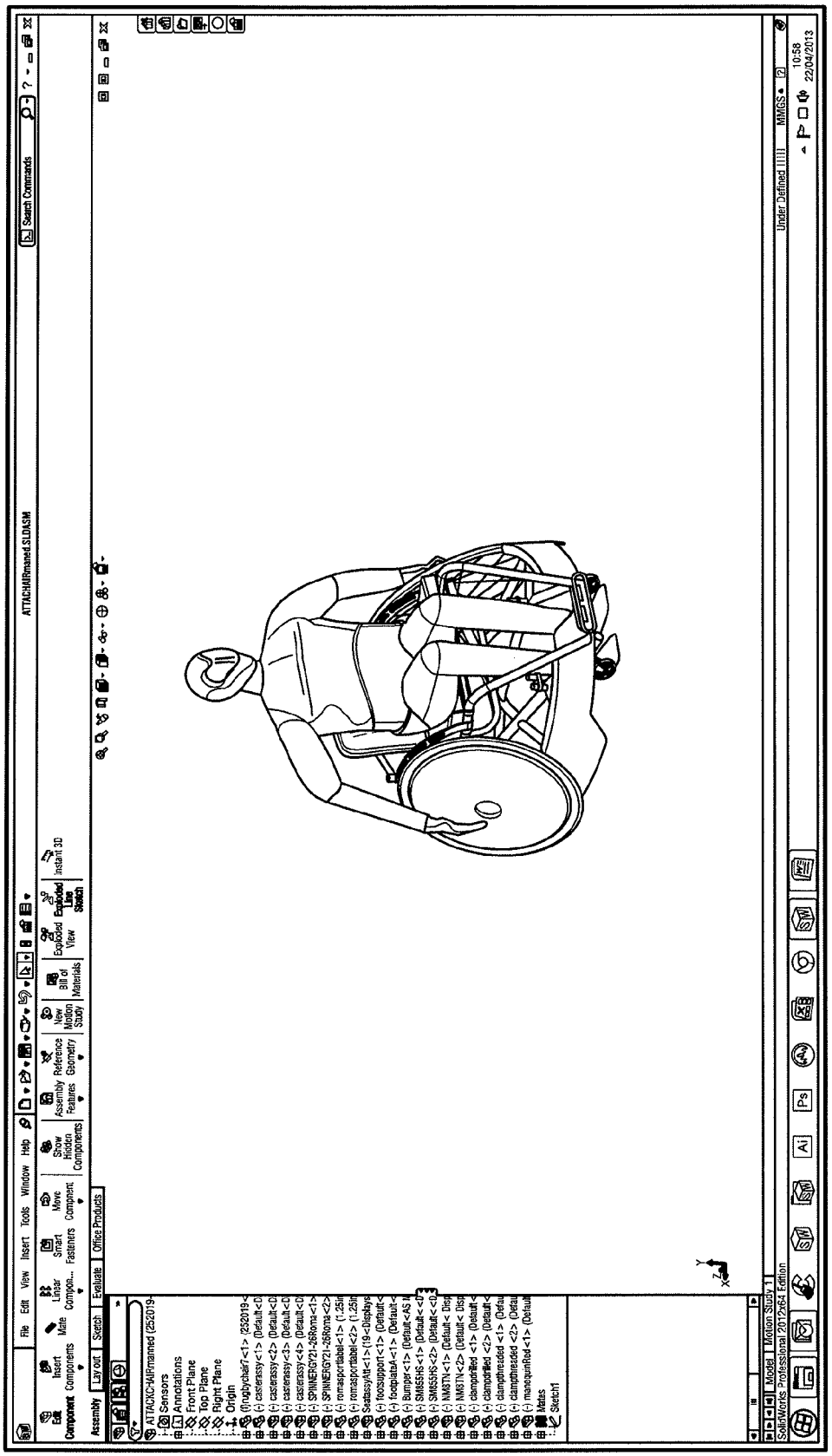
FIG. 6 shows a computer-generated representation of a user seated in a sports wheelchair having components corresponding to parameters derived from a measuring jig in accordance with the invention.
Figure 8:
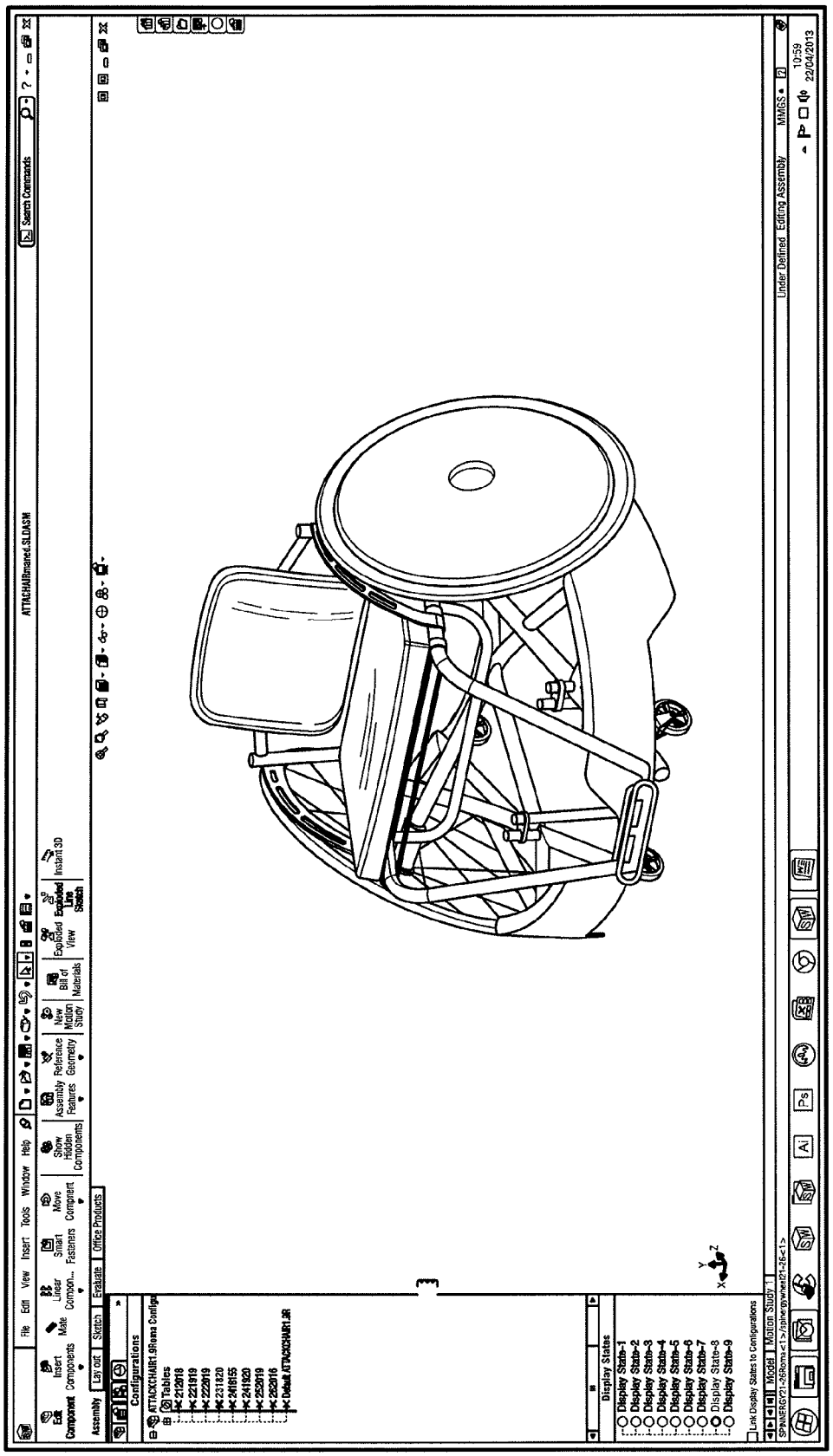
FIG. 8 shows a computer-generated representation of a sports wheelchair, the representation having been generated in accordance with an embodiment of the inventive system, and providing an indication of what the customised wheelchair would look like if manufactured according to the measurements obtained from the jig of the invention.

In such embodiments, the data gathered from the jig can then be used to produce a model (possibly 3-dimensional model) of the chair as it will look in its final form when constructed or adapted in accordance with the specified parameters (such as those in the table of FIG. 11). For example, FIGS. 6 and 8 show such a model of a sports wheelchair.

Figure 9:
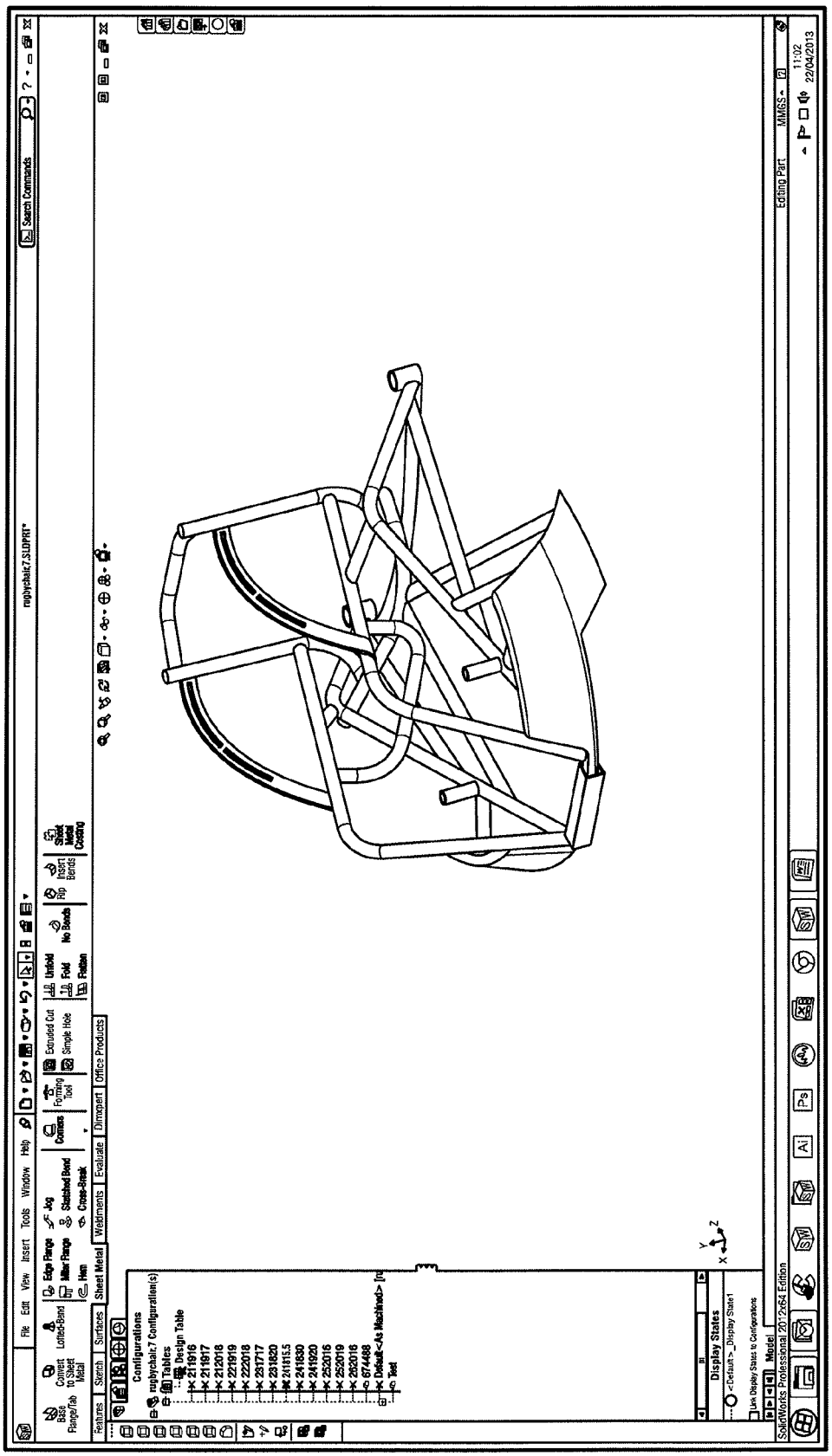
FIG. 9 shows the wheelchair of FIG. 8 in a stripped-down view, showing the frame and chair components as defined by the measured data.
Figure 10:
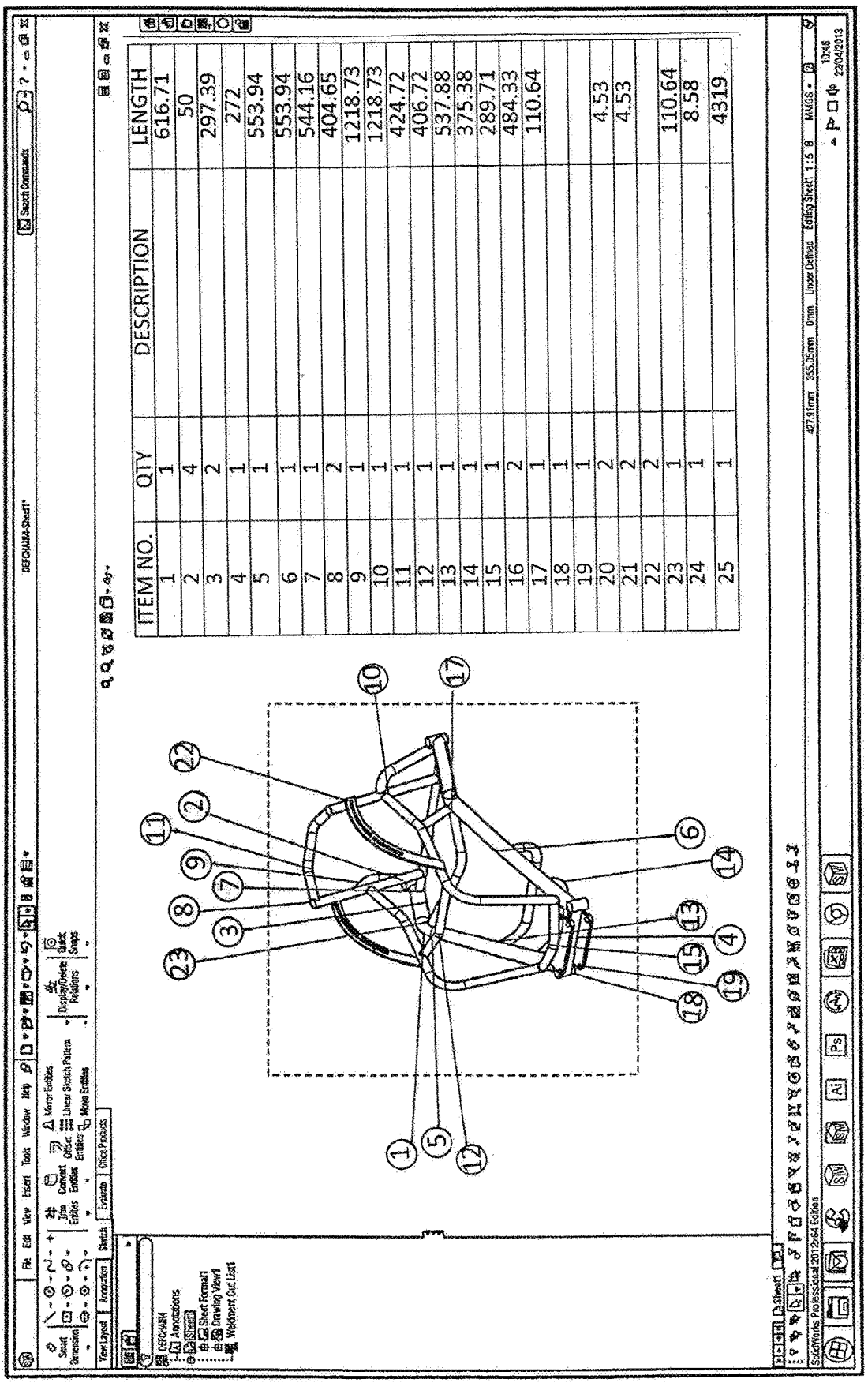
FIG. 10 shows the frame of FIG. 9 with the corresponding component data also shown.

The electronic information and/or the CAD model can be used in an automated manufacturing process in which the components for manufacturing the bespoke wheelchair in the required configuration can be selected, manufactured and assembled. FIG. 9 shows the wheelchair of FIGS. 6 and 8 in a stripped down view, showing the various components which make up the structure and frame. FIG. 10 shows the same frame but with the parameters for the components also shows. By altering the parameters, the model can be updated.

Figure 7:
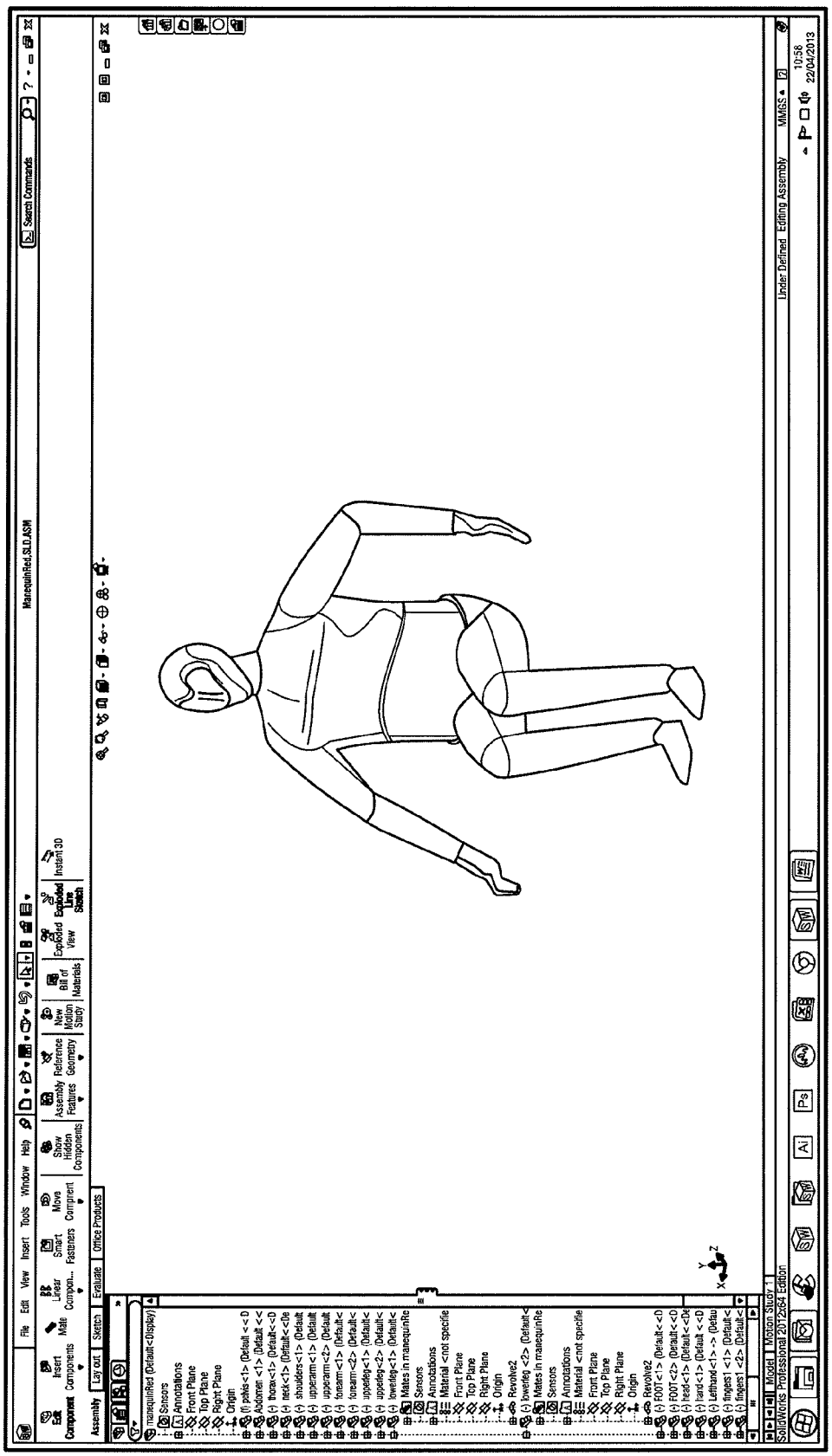
FIG. 7 shows a model of a wheelchair user, the user's measurements having been recorded and entered into a system in accordance with an embodiment of the invention.

In addition to modelling the customised chair, the user's measurements (e.g. leg length, height etc.) can be inputted into the system to generate a model of the user as shown in FIG. 7. The user can then be shown seated in the model of the customised chair, as illustrated in FIG. 6. This can be beneficial because the user is able to see how the specified chair will accommodate him. For example, if the representation shows the user's hands falling below an optimal position on the wheel of the chair, the seat height may need to be adjusted. Alternatively, for example, the representation may indicate that the user's knees will higher than desired and so the chair parameters can be adjusted until re-modelled until the user is happy with the image he is presented with.

Another advantage of the system is that it can be used to enforce or at least advise on regulations relating to the design of wheelchair components. These regulations may, for example, be legal requirements (such as health and safety legislation) or may be imposed by sporting bodies for sports wheelchairs. For example, the system may not permit a parameter to be entered for wheel diameter which is lower than the allowed minimum wheel size within a given sport.

Once all of the chair components have been adjusted according to the user's satisfaction, and the geometric data relating to those adjustments has been recorded, it can be used to build a new bespoke wheelchair (e.g. without adjustment means), or reconfigure an existing wheelchair, so that it corresponds to the 'ideal' configuration determined via usage of the jig.

For example a bespoke wheelchair can be manufactured to a set design using a standard range of components. Typically the components include frame members to be cut to a specific length and bent or otherwise shaped at certain angles. The present system enables the measured data from the jig and computer system to be used to create a build parts specification including specifying build component data such as length to cut frame members, bend angle and similar. It should be noted that the measurements are not simply substituted from the measurements taken but rather the computer system operates to translate the measurements taken according to a specific program related to the final design of wheelchair to create the build specification. The visual design of the bespoke wheelchair to be manufactured may bear no similarity to the design of the measuring jig.

Thus, the invention in all its embodiments provides a way of enabling a user to specify and forecast, through physical testing and provision of modelling and feedback, the precise set-up of a wheelchair; that specification can be easily delivered for manufacturing the appliance.

This eliminates the disappointment, inconvenience and financial loss suffered when the appliance has been configured in accordance with imprecise specifications.

The invention is not intended to be limited with regard to the number or type of adjustable components provided on the device, or on the type of wheelchair that is to be customised, or the number or type of measuring device which may be provided in, on or in association with the invention.

It should be noted that the above-mentioned embodiments illustrate rather than limit the invention, and that those skilled in the art will be capable of designing many alternative embodiments without departing from the scope of the invention as defined by the appended claims. In the claims, any reference signs placed in parentheses shall not be construed as limiting the claims. The word "comprising" and "comprises", and the like, does not exclude the presence of elements or steps other than those listed in any claim or the specification as a whole. In the present specification, "comprises" means "includes or consists of" and "comprising" means "including or consisting of". The singular reference of an element does not exclude the plural reference of such elements and vice-versa. The mere fact that certain measures are recited in mutually different dependent claims does not indicate that a combination of these measures cannot be used to advantage.

The invention claimed is:
1. A method of specifying a configuration of a customized wheelchair for a user, the method comprising:
  i) providing a measurement jig comprising a plurality of adjustable components that enable derivation of a plurality of measurements related to a bespoke configuration of the customized wheelchair, wherein the measurement jig is configured to seat the user, wherein at least one adjustable component of the plurality adjustable components is manually adjustable by hand to enable at least one measurement of the plurality of measurements to be manually taken, and wherein the measurement jig is configured to only permit measurements which fit within an acceptable range for each adjustable component;
  ii) using the measurement jig to derive a plurality of measurements relating to size, position, orientation or configuration of the adjustable components of the measurement jig while the user is seated in the measurement jig and at least one of the adjustable components of the measurement jig is adjusted around the user, wherein at least one measurement of the plurality of measurements is derived while manually adjusting at least one manually adjustable component of the measurement jig by hand;
  iii) automatically feeding data relating to the plurality of measurements derived by the measurement jig as input to a computer-implemented model generation device;
  iv) configuring the computer-implemented model generation device to generate a visual representation of the user seated in the bespoke configuration of the customized wheelchair based on the data relating to the plurality of measurements derived by the measurement jig and input to the computer-implemented model generation device;

v) displaying the visual representation of the user seated in the bespoke configuration of the customized wheelchair for viewing by the user;

vi) receiving a user feedback related to fit of the bespoke configuration of the customized wheelchair based on the visual representation;

vii) using the measurement jig to derive at least one additional measurement relating to size, position, orientation or configuration of the adjustable components of the measurement jig while the user is seated in the measurement jig and at least one of the adjustable components of the measurement jig is adjusted around the user based on the user feedback related to fit of the bespoke configuration of the customized wheelchair;

viii) automatically feeding data relating to the at least one additional measurement derived by the measurement jig in vii) as input to the computer-implemented model generation device;

ix) configuring the computer-implemented model generation device to generate an additional visual representation of the user seated in the bespoke configuration of the customized wheelchair based on the data relating to the at least one additional measurement derived by the measurement jig in vii) and input to the computer-implemented model generation device in viii); and x) displaying the additional visual representation of the user seated in the bespoke configuration of the customized wheelchair of ix) for viewing by the user.

2. A method according to claim 1, wherein the manual adjustment of the at least one manually adjustable component of the measurement jig in ii) is performed in response to one or more instructions received from the user.

3. A method according to claim 1, further comprising:
recording or communicating the data relating to the plurality of measurements derived by the measurement jig as well as the data relating to the at least one additional measurement derived by the measurement jig for use in construction, reconfiguration, or computerized modeling of the customized wheelchair.

4. The method according to claim 1, further comprising:
using the data relating to the plurality of measurements derived by the measurement jig as well as the data relating to the at least one additional measurement derived by the measurement jig to generate a component specification for manufacturing a specific design of the customized wheelchair.

5. The method according to claim 1, wherein:
the visual representation of the user seated in the bespoke configuration of the customized wheelchair of v) comprises a 2-D image or a 3-D model; and
the additional visual representation of the user seated in the bespoke configuration of the customized wheelchair of ix) comprises a 2-D image or a 3-D model.

6. The method according to claim 1, wherein:
at least one of the manually adjustable components comprises a backrest adjustable in each of the horizontal and vertical directions and also tiltable between an upright position and an inclined position.

* * * * *